(12) United States Patent
Parikh et al.

(10) Patent No.: US 9,237,860 B2
(45) Date of Patent: Jan. 19, 2016

(54) MOTION COMPENSATION FOR MEDICAL IMAGING AND ASSOCIATED SYSTEMS AND METHODS

(75) Inventors: Parag J. Parikh, St. Louis, MO (US); Steven C. Dimmer, Bellevue, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 350 days.

(21) Appl. No.: 12/996,448

(22) PCT Filed: Jun. 5, 2009

(86) PCT No.: PCT/US2009/046494
§ 371 (c)(1),
(2), (4) Date: Jun. 28, 2011

(87) PCT Pub. No.: WO2009/149409
PCT Pub. Date: Dec. 10, 2009

(65) Prior Publication Data
US 2011/0249880 A1 Oct. 13, 2011

Related U.S. Application Data

(60) Provisional application No. 61/059,119, filed on Jun. 5, 2008.

(51) Int. Cl.
G06K 9/00 (2006.01)
A61B 5/06 (2006.01)
(Continued)

(52) U.S. Cl.
CPC .................. *A61B 5/06* (2013.01); *A61B 5/1127* (2013.01); *A61B 6/032* (2013.01); *A61B 6/025* (2013.01); *A61B 6/027* (2013.01); *A61B 6/482* (2013.01); *A61B 6/583* (2013.01); *A61N 5/1037* (2013.01)

(58) Field of Classification Search
None
See application file for complete search history.

(56) References Cited

U.S. PATENT DOCUMENTS 3,967,161 A 6/1976 Lichtblau
4,017,858 A 4/1977 Kuipers
(Continued)

FOREIGN PATENT DOCUMENTS

DE 19914455 10/2000
EP 0531081 A1 3/1993
(Continued)

OTHER PUBLICATIONS

Beyer, Thomas, et al. "Dual-modality PET/CT imaging: the effect of respiratory motion on combined image quality in clinical oncology." European journal of nuclear medicine and molecular imaging 30.4 (2003): 588-596.*
(Continued)

*Primary Examiner* — Bhavesh Mehta
*Assistant Examiner* — Sean Conner
(74) *Attorney, Agent, or Firm* — Perkins Coie LLP

(57) ABSTRACT

Medical imaging and localization methods and systems for producing a motion-compensated image of a planning target volume (PTV) of a patient. In one embodiment, an imaging and localization system includes sensors that are positioned to receive an electromagnetic location signal from one or more active markers affixed to or adjacent a PTV. A signal processing component can produce real-time localization data corresponding to the location signal, and a system interface can receive such localization data. The system interface can also receive raw image data from an imaging subsystem and process the raw image data based on the localization data. For example, the imaging subsystem can include a computed tomography (CT) imaging system and image slices or frames can be binned based on the localization data.

21 Claims, 12 Drawing Sheets

(51) Int. Cl.
  *A61B 5/11*  (2006.01)
  *A61B 6/03*  (2006.01)
  *A61B 6/02*  (2006.01)
  *A61B 6/00*  (2006.01)
  *A61N 5/10*  (2006.01)

(56) References Cited

U.S. PATENT DOCUMENTS

| | | |
|---|---|---|
| 4,023,167 A | 5/1977 | Wahlstrom |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,343,196 A | 8/1982 | Wirth et al. |
| 4,393,872 A | 7/1983 | Reznik et al. |
| 4,466,075 A | 8/1984 | Groch |
| 4,618,822 A | 10/1986 | Hansen |
| 4,633,250 A | 12/1986 | Anderson, III et al. |
| 4,642,786 A | 2/1987 | Hansen |
| 4,643,196 A | 2/1987 | Tanaka et al. |
| 4,696,287 A | 9/1987 | Hortmann et al. |
| 4,737,794 A | 4/1988 | Jones |
| 4,795,995 A | 1/1989 | Eccleston et al. |
| 4,799,495 A | 1/1989 | Hawkins et al. |
| 4,849,692 A | 7/1989 | Blood |
| 4,909,789 A | 3/1990 | Taguchi et al. |
| 4,936,823 A | 6/1990 | Colvin et al. |
| 4,945,305 A | 7/1990 | Blood |
| 4,945,914 A | 8/1990 | Allen |
| 4,994,079 A | 2/1991 | Genese et al. |
| 5,031,634 A | 7/1991 | Simon |
| 5,050,608 A | 9/1991 | Watanabe |
| 5,062,847 A | 11/1991 | Barnes |
| 5,095,224 A | 3/1992 | Renger et al. |
| 5,099,845 A | 3/1992 | Besz et al. |
| 5,107,862 A | 4/1992 | Fabian et al. |
| 5,117,829 A | 6/1992 | Miller et al. |
| 5,142,292 A | 8/1992 | Chang |
| 5,170,055 A | 12/1992 | Carroll et al. |
| 5,188,368 A | 2/1993 | Ryan et al. |
| 5,198,877 A | 3/1993 | Schulz |
| 5,221,269 A | 6/1993 | Miller |
| 5,222,499 A | 6/1993 | Allen et al. |
| 5,240,011 A | 8/1993 | Assa |
| 5,325,873 A | 7/1994 | Hirschi et al. |
| 5,353,804 A | 10/1994 | Kornberg et al. |
| 5,377,678 A | 1/1995 | Dumoulin |
| 5,397,329 A | 3/1995 | Allen |
| 5,409,004 A | 4/1995 | Sloan |
| 5,411,026 A | 5/1995 | Carol |
| 5,417,210 A | 5/1995 | Funda |
| 5,423,334 A | 6/1995 | Jordan |
| 5,425,367 A | 6/1995 | Shapiro et al. |
| 5,425,382 A | 6/1995 | Golden et al. |
| 5,431,161 A | 7/1995 | Ryals et al. |
| 5,446,548 A | 8/1995 | Gerig |
| 5,453,686 A | 9/1995 | Anderson |
| 5,509,900 A | 4/1996 | Kirkman |
| 5,515,853 A | 5/1996 | Smith |
| 5,526,812 A | 6/1996 | Dumoulin et al. |
| 5,528,651 A | 6/1996 | Leksell et al. |
| 5,546,951 A | 8/1996 | Ben-Haim |
| 5,558,091 A | 9/1996 | Acker |
| 5,568,809 A | 10/1996 | Ben-Haim |
| 5,572,999 A | 11/1996 | Funda et al. |
| 5,617,857 A | 4/1997 | Chader |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,638,819 A | 6/1997 | Manwaring et al. |
| 5,680,106 A | 10/1997 | Schrott et al. |
| 5,681,326 A | 10/1997 | Lax |
| 5,697,384 A | 12/1997 | Miyawaki et al. |
| 5,707,362 A | 1/1998 | Yoon |
| 5,707,390 A | 1/1998 | Bonutti |
| 5,727,552 A | 3/1998 | Ryan |
| 5,735,795 A | 4/1998 | Young et al. |
| 5,745,545 A | 4/1998 | Hughes |
| RE35,816 E | 6/1998 | Schulz |
| 5,764,052 A | 6/1998 | Renger |
| 5,769,861 A | 6/1998 | Vilsmeier et al. |
| 5,779,638 A | 7/1998 | Vesely |
| 5,797,849 A | 8/1998 | Vesely et al. |
| 5,805,661 A | 9/1998 | Leksell |
| 5,810,851 A | 9/1998 | Yoon |
| 5,815,076 A | 9/1998 | Herring |
| 5,817,022 A | 10/1998 | Vesely |
| 5,820,553 A | 10/1998 | Hughes |
| 5,823,192 A | 10/1998 | Kalend et al. |
| 5,828,770 A | 10/1998 | Leis et al. |
| 5,830,144 A | 11/1998 | Vesely |
| 5,840,148 A | 11/1998 | Campbell et al. |
| 5,868,673 A | 2/1999 | Vesely |
| 5,868,675 A | 2/1999 | Henrion et al. |
| 5,879,297 A | 3/1999 | Haynor et al. |
| 5,879,357 A | 3/1999 | Heaton |
| 5,899,857 A | 5/1999 | Wilk |
| 5,902,238 A | 5/1999 | Golden |
| 5,902,310 A | 5/1999 | Foerster |
| 5,910,144 A | 6/1999 | Hayashi |
| 5,913,820 A | 6/1999 | Bladen |
| 5,923,417 A | 7/1999 | Leis |
| 5,928,137 A | 7/1999 | Green |
| 5,951,481 A | 9/1999 | Evans |
| 5,987,349 A | 11/1999 | Schulz |
| 5,989,265 A | 11/1999 | Bouquet De La Joliniere et al. |
| 6,015,390 A | 1/2000 | Krag |
| 6,019,725 A | 2/2000 | Vesely et al. |
| 6,026,818 A | 2/2000 | Blair et al. |
| 6,049,587 A | 4/2000 | Leksell et al. |
| 6,052,477 A | 4/2000 | Wang et al. |
| 6,059,734 A | 5/2000 | Yoon |
| 6,061,644 A | 5/2000 | Leis |
| 6,064,904 A | 5/2000 | Yanof et al. |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra et al. |
| 6,094,007 A | 7/2000 | Faul |
| 6,097,994 A | 8/2000 | Navab |
| 6,118,848 A * | 9/2000 | Reiffel ............................ 378/65 |
| 6,144,875 A | 11/2000 | Schweikard |
| 6,161,009 A | 12/2000 | Skurdal et al. |
| 6,173,715 B1 | 1/2001 | Sinanan et al. |
| 6,198,963 B1 | 3/2001 | Haim et al. |
| 6,239,724 B1 | 5/2001 | Doron et al. |
| 6,246,900 B1 | 6/2001 | Cosman et al. |
| 6,307,473 B1 | 10/2001 | Zampini et al. |
| 6,325,758 B1 | 12/2001 | Carol et al. |
| 6,363,940 B1 | 4/2002 | Krag |
| 6,371,379 B1 | 4/2002 | Dames et al. |
| 6,381,485 B1 | 4/2002 | Hunter et al. |
| 6,401,722 B1 | 6/2002 | Krag |
| 6,405,072 B1 | 6/2002 | Cosman |
| 6,416,520 B1 | 7/2002 | Kynast et al. |
| 6,474,341 B1 | 11/2002 | Hunter et al. |
| 6,611,700 B1 | 8/2003 | Vilsmeier et al. |
| 6,675,810 B2 | 1/2004 | Krag |
| 6,698,433 B2 | 3/2004 | Krag |
| 6,812,842 B2 | 11/2004 | Dimmer |
| 6,822,570 B2 | 11/2004 | Dimmer et al. |
| 6,838,990 B2 | 1/2005 | Dimmer |
| 6,918,919 B2 | 7/2005 | Krag |
| 6,963,770 B2 | 11/2005 | Scarantino et al. |
| 7,135,978 B2 | 11/2006 | Gisselberg et al. |
| 7,657,301 B2 | 2/2010 | Mate et al. |
| 7,657,302 B2 | 2/2010 | Mate et al. |
| 7,657,303 B2 | 2/2010 | Mate et al. |
| 2002/0065461 A1 | 5/2002 | Cosman |
| 2002/0193685 A1 | 12/2002 | Mate et al. |
| 2003/0088178 A1 | 5/2003 | Owens et al. |

(56) References Cited

U.S. PATENT DOCUMENTS

| | | |
|---|---|---|
| 2003/0192557 A1 | 10/2003 | Krag et al. |
| 2003/0206614 A1 | 11/2003 | Kendrick et al. |
| 2004/0092815 A1 | 5/2004 | Schweikard et al. |
| 2004/0123871 A1 | 7/2004 | Wright et al. |
| 2004/0125916 A1 | 7/2004 | Herron et al. |
| 2004/0133101 A1 | 7/2004 | Mate |
| 2004/0138555 A1 | 7/2004 | Krag |
| 2004/0158146 A1 | 8/2004 | Mate |
| 2004/0176931 A1 | 9/2004 | Wright |
| 2004/0236207 A1 | 11/2004 | Widener et al. |
| 2005/0059884 A1 | 3/2005 | Krag |
| 2005/0140372 A1* | 6/2005 | Wright et al. ............ 324/326 |
| 2005/0154280 A1 | 7/2005 | Wright et al. |
| 2005/0154293 A1 | 7/2005 | Gisselberg |
| 2005/0195084 A1 | 9/2005 | Dimmer et al. |
| 2005/0201510 A1* | 9/2005 | Mostafavi ................ 378/8 |
| 2005/0261570 A1* | 11/2005 | Mate et al. .............. 600/411 |
| 2006/0074301 A1 | 4/2006 | Meier et al. |
| 2006/0074302 A1 | 4/2006 | Meier et al. |
| 2006/0079764 A1* | 4/2006 | Wright et al. ............ 600/431 |
| 2006/0173294 A1* | 8/2006 | Ein-Gal ................... 600/427 |
| 2007/0153972 A1 | 7/2007 | Fujishige et al. |
| 2008/0039746 A1 | 2/2008 | Hissong et al. |
| 2008/0226149 A1* | 9/2008 | Wischmann et al. ...... 382/131 |
| 2011/0046481 A1 | 2/2011 | Mate et al. |

FOREIGN PATENT DOCUMENTS

| | | |
|---|---|---|
| EP | 0 719 420 | 11/1999 |
| EP | 1 034 738 | 9/2000 |
| FR | 2635259 | 2/1990 |
| FR | 2686499 A1 | 7/1993 |
| JP | 8-166446 | 6/1996 |
| WO | WO-88/08282 | 11/1988 |
| WO | WO-95/25475 | 9/1995 |
| WO | WO-95/33519 A1 | 12/1995 |
| WO | WO-96/08208 | 3/1996 |
| WO | WO-96/08999 | 3/1996 |
| WO | WO-97/12553 | 4/1997 |
| WO | WO-97/36192 | 10/1997 |
| WO | WO-97/48438 | 12/1997 |
| WO | WO-98/30166 | 7/1998 |
| WO | WO-98/38908 | 9/1998 |
| WO | WO-98/40026 | 9/1998 |
| WO | WO-99/17133 | 4/1999 |
| WO | WO-99/27839 | 6/1999 |
| WO | WO-99/30182 | 6/1999 |
| WO | WO-99/33406 A1 | 7/1999 |
| WO | WO-99/35966 | 7/1999 |
| WO | WO-99/40869 | 8/1999 |
| WO | WO-9953966 A1 | 10/1999 |
| WO | WO-99/58044 | 11/1999 |
| WO | WO-99/58055 | 11/1999 |
| WO | WO-99/58065 | 11/1999 |
| WO | WO-00/24332 | 5/2000 |
| WO | WO-00/38579 | 7/2000 |
| WO | WO-00/51514 | 9/2000 |
| WO | WO-00/53115 A1 | 9/2000 |
| WO | WO-00/65989 | 11/2000 |
| WO | WO-01/34049 | 5/2001 |
| WO | WO-01/54765 | 8/2001 |
| WO | WO-02/19908 | 3/2002 |
| WO | WO-02/39917 A1 | 5/2002 |
| WO | WO-02/39918 | 5/2002 |
| WO | WO-02/100485 | 12/2002 |
| WO | WO-2006113323 A2 | 10/2006 |

OTHER PUBLICATIONS

Low, Daniel A., et al. "A method for the reconstruction of four-dimensional synchronized CT scans acquired during free breathing." Medical physics 30.6 (2003): 1254-1263.*

Wolthaus, J. W. H., et al. "Fusion of respiration-correlated PET and CT scans: correlated lung tumour motion in anatomical and functional scans." Physics in medicine and biology 50.7 (2005): 1569.*

U.S. Appl. No. 10/416,827, Krag.

Final Office Action, U.S. Appl. No. 09/877,498, Applicant: Calypso Medical Technologies, Inc., Date of Mailing: Feb. 14, 2006, 7 pages.

Decision on Appeal, U.S. Appl. No. 09/877,498, Applicant: Calypso Medical Technologies, Inc., Date of Mailing: May 27, 2009, 16 pages.

Final Office Action; U.S. Appl. No. 09/877,498; Applicant: Calypso Medical Technologies, Inc.; Date of Mailing: Feb. 14, 2006; 7 pages.

Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science, pp. 1-107.

International Preliminary Examination Report; PCT/US02/17876, filed Jun. 5, 2002, in the name of Calypso Medical Technologies, Inc.

International Search Report dated Jan. 24, 2003, PCT Application No. PCT/US/29390.

European Search Report dated Jun. 28, 2011, EP Application No. 10185512.

International Search Report and Written Opinion dated Jul. 28, 2009, PCT Application No. US09/046494, 12 pages.

\* cited by examiner

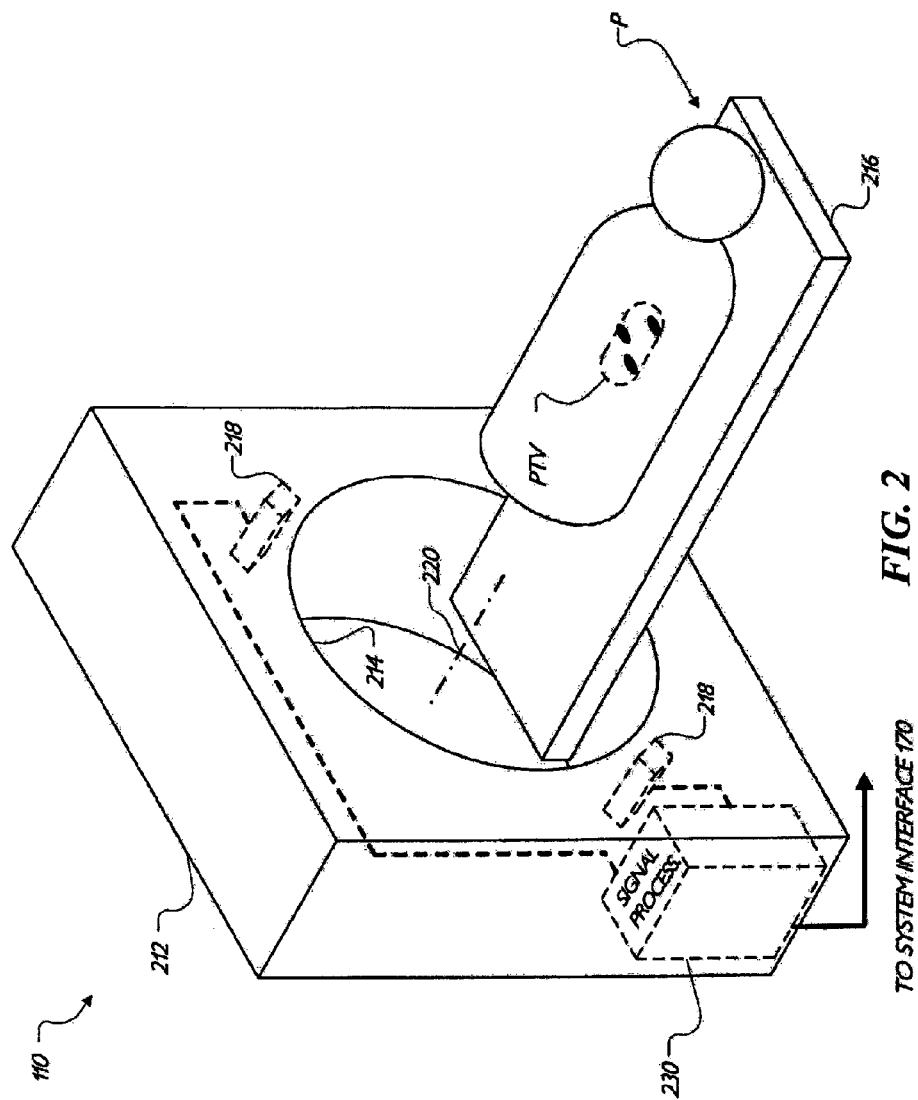

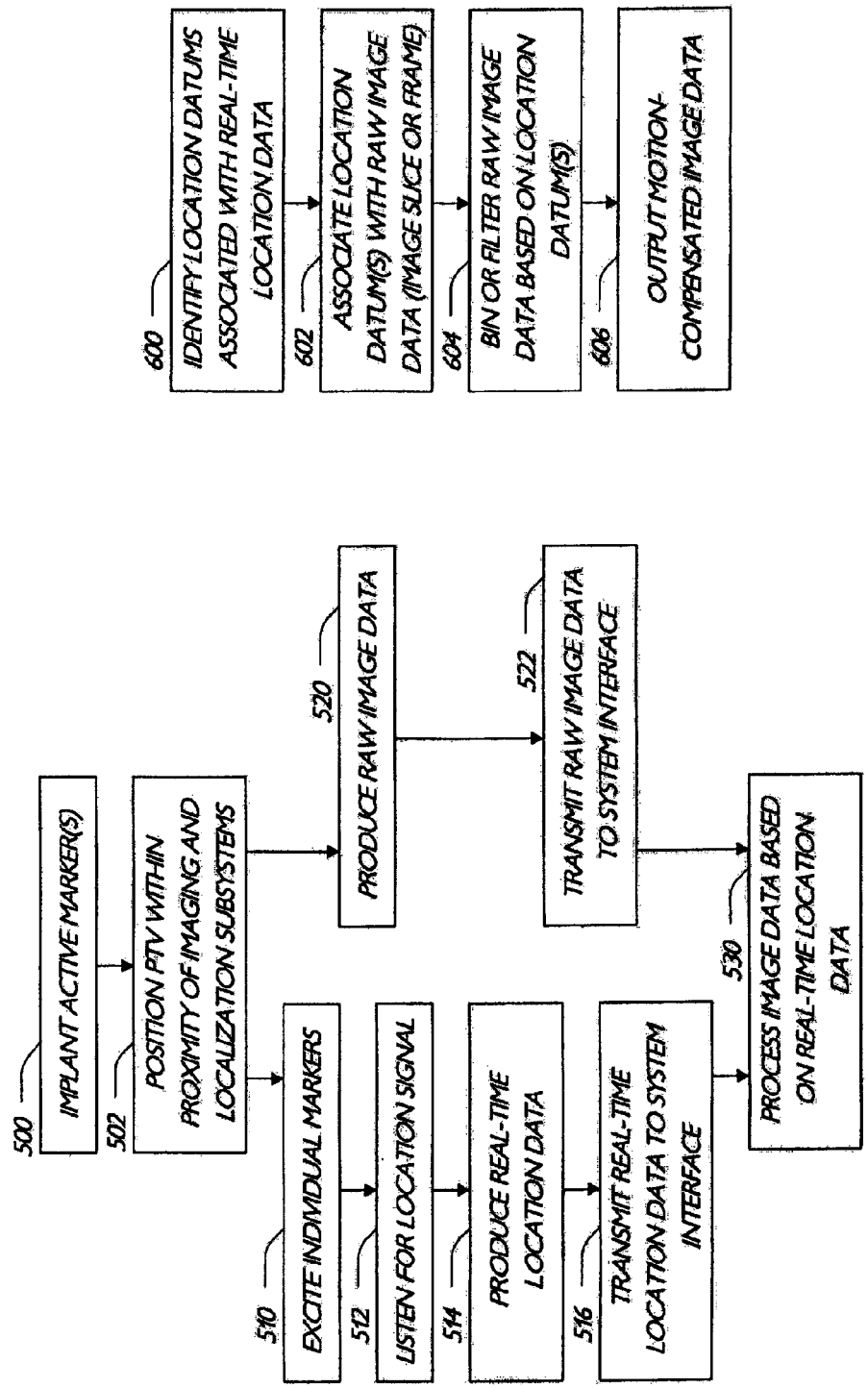

MOTION COMPENSATION FOR MEDICAL IMAGING AND ASSOCIATED SYSTEMS AND METHODS

CROSS-REFERENCE TO RELATED APPLICATIONS

This application is a U.S. National Phase of International Patent Application No. PCT/US2009/046494, filed Jun. 5, 2009, and titled MOTION COMPENSATION FOR MEDICAL IMAGING AND ASSOCIATED SYSTEMS AND METHODS, which claims the benefit of U.S. Provisional Patent Application No. 61/059,119, filed Jun. 5, 2008, and titled MOTION COMPENSATION FOR MEDICAL IMAGING AND ASSOCIATED SYSTEMS AND METHODS; the disclosure of each of these applications is incorporated herein by reference in its entirety.

TECHNICAL FIELD

The present disclosure is generally related to systems and methods for compensating for patient motion in medical imaging applications.

BACKGROUND

In medical imaging of the thoracic cavity, intrafraction movement can have a significant effect on medical imaging quality. Intrafraction movement occurs when the patient and/or organs within the thoracic cavity (e.g., lungs, heart, etc.) move during an imaging scan. Respiratory movement, in particular, can have a significant affect on image quality and can produce a variety of artifacts (e.g., blur, distortion, etc.) within a medical image. These imaging artifacts can in turn affect the extent to which medical practitioners can rely on a medical image for diagnoses or for treatment planning. For example, in order to compensate for any uncertainties created by imaging artifacts, radiologists may need to over estimate a target treatment volume in a patient.

In general, there exist several techniques to account for respiratory motion in medical imaging. For example, these techniques can including breath-hold, respiratory gating or breathing coaching, which employs visual and/or audio feedback regarding when a patient should inhale and/or exhale. By controlling a patient's breathing in either of these manners, the amount of image artifacts can be reduced to an extent. Unfortunately, however, such breath-hold and coaching techniques are limited. For example, only about 40% of the lung cancer population can hold their breath for an adequate duration of time, and breathing coaching cannot account for irregular motion of the lungs (or irregular motion of tissues adjacent the lungs).

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 2 is an isometric, schematic diagram of the system of FIG. 1 showing an embodiment of an imaging subsystem in more detail.

FIG. 5 is a flow diagram of a method of operating the system of FIG. 1.

FIG. 6 is a flow diagram of an embodiment of a method for binning or filtering raw image data of an imaging subsystem based on real-time localization data of a localization subsystem.

DETAILED DESCRIPTION

A. System Overview

The following disclosure is directed towards compensating for intrafraction movement in medical imaging systems, for example, compensating for respiratory motion in 4-dimensional computed tomography (CT) imaging systems, including axial CT, helical CT, and ciné CT imaging systems. Well-known characteristics often associated with medical imaging systems and associated signal/data processing have not been shown or described in detail to avoid unnecessarily obscuring the description of the various embodiments. Those of ordinary skill in the relevant art will understand that additional embodiments may be practiced without several of the details described below, and that other embodiments may include aspects in addition to those described below.

Figure 1A:
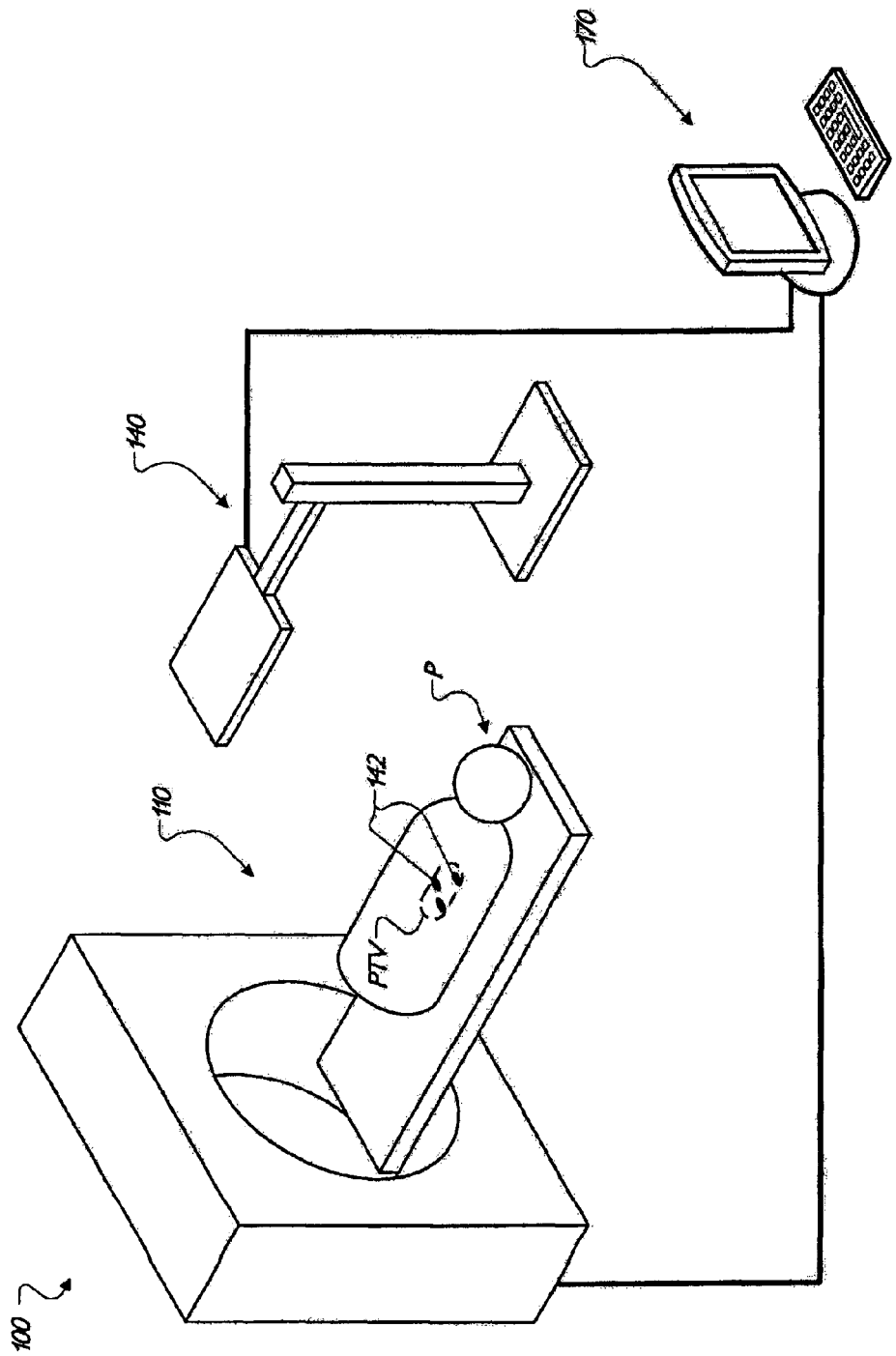
FIGS. 1A and 1B are isometric, schematic diagrams of an imaging and localization system configured in accordance with an embodiment of the disclosure.

FIG. 1A is a schematic diagram illustrating a representative embodiment of an imaging and localization system 100. The system 100 can include an imaging subsystem 110, a localization subsystem 140, and a system interface 170 operably coupled to the imaging and localization subsystems 110 and 140. In operation, the imaging subsystem 110 produces raw image data by scanning a planning target volume (PTV) within a patient. The raw image data can include image slices or image frames (e.g., raw image data computed from multiple image slices). The PTV, for example, can be a portion of an organ and/or tissue within the thoracic cavity of the patient (e.g., a lung, tumor, etc.).

The localization subsystem 140, in operation, employs one or more (implantable) active markers 142 adjacent the PTV that can be tracked or monitored. The active markers, for example, are electrically active, generating detectable electromagnetic pulses when excited by an external source (described further with reference to FIG. 3). When positioned within range of individual markers 142, the localization system 140 can track the real-time location of these markers, and thus can also track the real-time location of the PTV. In many embodiments, and described in more detail below, the localization subsystem 140 tracks the real-time location of the PTV, while the imaging subsystem 110 concurrently scans the PTV.

Figure 1B:
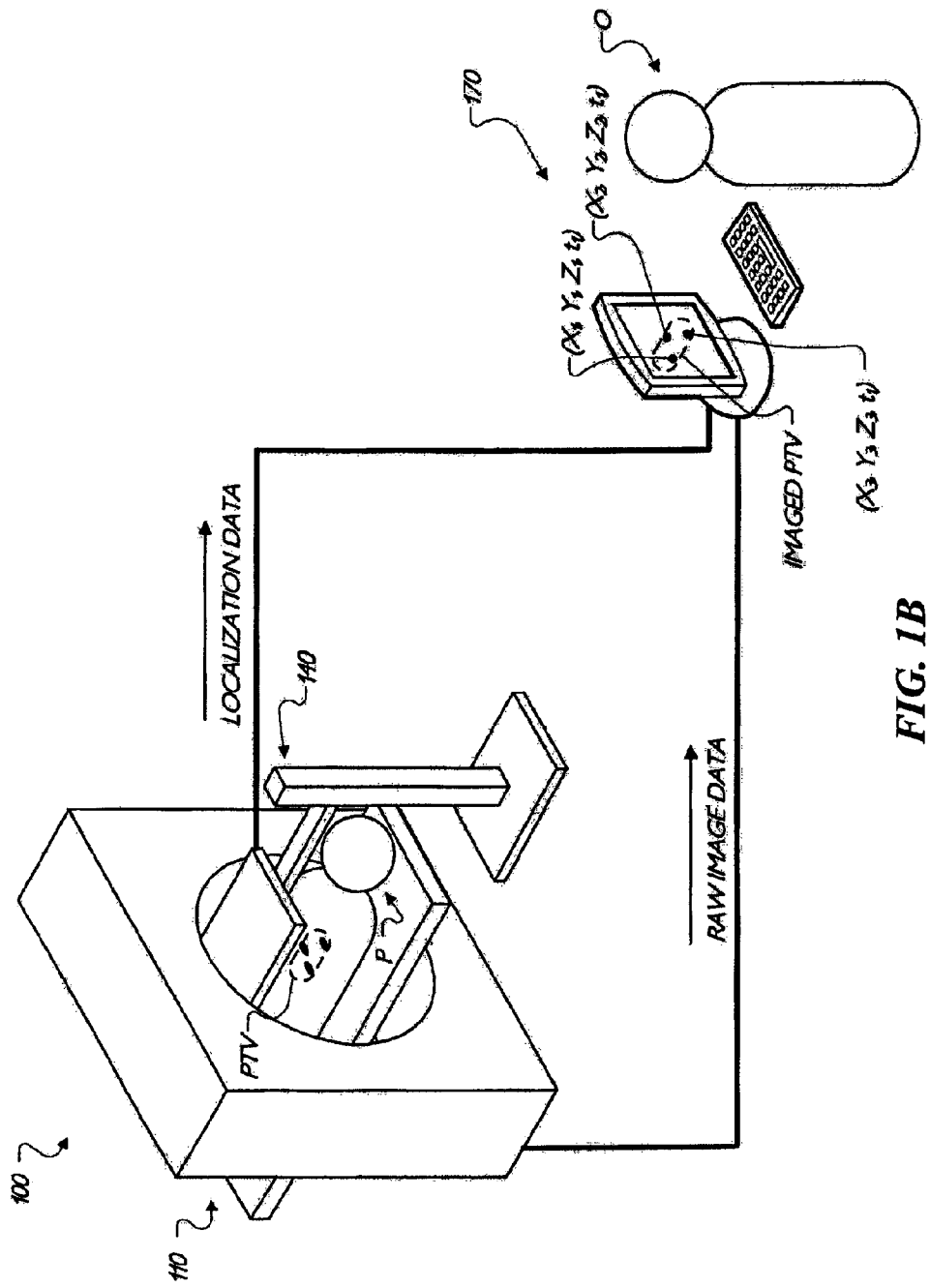

FIG. 1B is a schematic diagram illustrating the system 100 and, more specifically, the localization system 140 and the patient (including the PTV) positioned within the imaging system 110. When positioned in such a manner, the imaging and localization subsystems 110 and 140 can concurrently produce and transmit both raw image data of the PTV and real-time localization data regarding the PTV to the system interface 170. The system interface 170 (e.g., a computer and/or operator station) can in turn (a) receive the raw image data and the real-time localization data, and (b) filter, bin, or otherwise process the raw image data based on the real-time localization data. In particular, the system interface 170 can yield motion-compensated image data that is synchronized with the real-time location of the PTV. Such synchronization mitigates or eliminates imaging artifacts in the image data, resulting in high quality image data that can be used or evaluated in combination with a variety of diagnostic and/or treatment planning procedures.

In contrast to the system 100, conventional imaging systems are limited by conventional techniques for (intrafraction) motion compensation. For example, as described above, breath-hold, respiratory gating can only be used on a minority of the cancer patient population, and breathing coaching can at best only account for predicable types of respiratory motion. Furthermore, other types of motion compensation techniques can only provide coarse approximations of a PTV location. For example, one conventional technique employs surrogate markers that are externally affixed to a patient's chest or abdomen, at a location that roughly corresponds with the internal location of a PTV. An Infrared radiation source can be used to illuminate the surrogate markers, and a video camera can use reflected radiation to track the movement of the surrogate. Although providing a rough approximation of respiratory motion, surrogate markers are not directly located at the PTV, and thus they are limited in accuracy. For example, during a patient's breathing cycle, the distance between the PTV and the surrogate markers can vary non-linearly and/or unpredictably. Surrogate markers cannot account for these non-linear and unpredictable types of motion. Consequently, in many surrogate marker techniques, the localization data is a predictive measure that determines a suitable gating window. For example, such a gating window can predict the times at which a patient's lungs should be in an inhaled or exhaled state, and raw image data can accordingly be gathered when the lungs are in either of these states. However, if a patient's breathing deviates from this predicted cycle, the raw image data loses accuracy.

Another conventional motion compensation technique includes implanting opaque fiducials at a PTV and correlating fiducial motion with the motion of surrogate markers. For example, a PTV can be imaged for a first period of time, and the location of the fiducials can be separately assessed during a second period of time. This process can be repeated until a motion map of the PTV is acquired, for example, by imaging once every 10 seconds and monitoring the fiducials between the imaging intervals. Generally, this type of motion compensation technique is complicated, has time-intensive set-up procedures, and is only effective for a minority of patients. Furthermore, the fiducial motion is not captured in real-time, nor does the fiducial motion represent accurate organ or tissue motion over relatively short time intervals (e.g., for intervals that are less than 10 seconds).

Embodiments of the imaging and localization system 100, however, overcome these and other limitations associated with conventional motion compensation techniques. For example, the raw image data of the system 100 can be processed based on the real-time PTV position and not exclusively on the predicted or approximated position of the PTV (i.e., derived by surrogate markers or from breath coaching techniques). Accordingly, the system 100 can account for a variety of non-linearities and unpredictable motion of the PTV. In addition, individual markers can transmit a unique electromagnetic signal, allowing the system interface 130 to identify and distinguish between individual markers. Surrogate markers and opaque fiducials, on the other hand, can only be discriminated optically with complicated and manually-intensive imaging procedures. Furthermore, unlike externally positioned surrogate markers, which can be inadvertently repositioned (e.g., by physical contact with the surrogate marker), implantable markers generally remain fixed to soft tissue within a patient and move with motion of soft tissue that they are rigidly fixed to. Accordingly, the implantable markers can reduce or eliminate patient-setup positioning errors.

B. System Components and Operation

Figure 3:
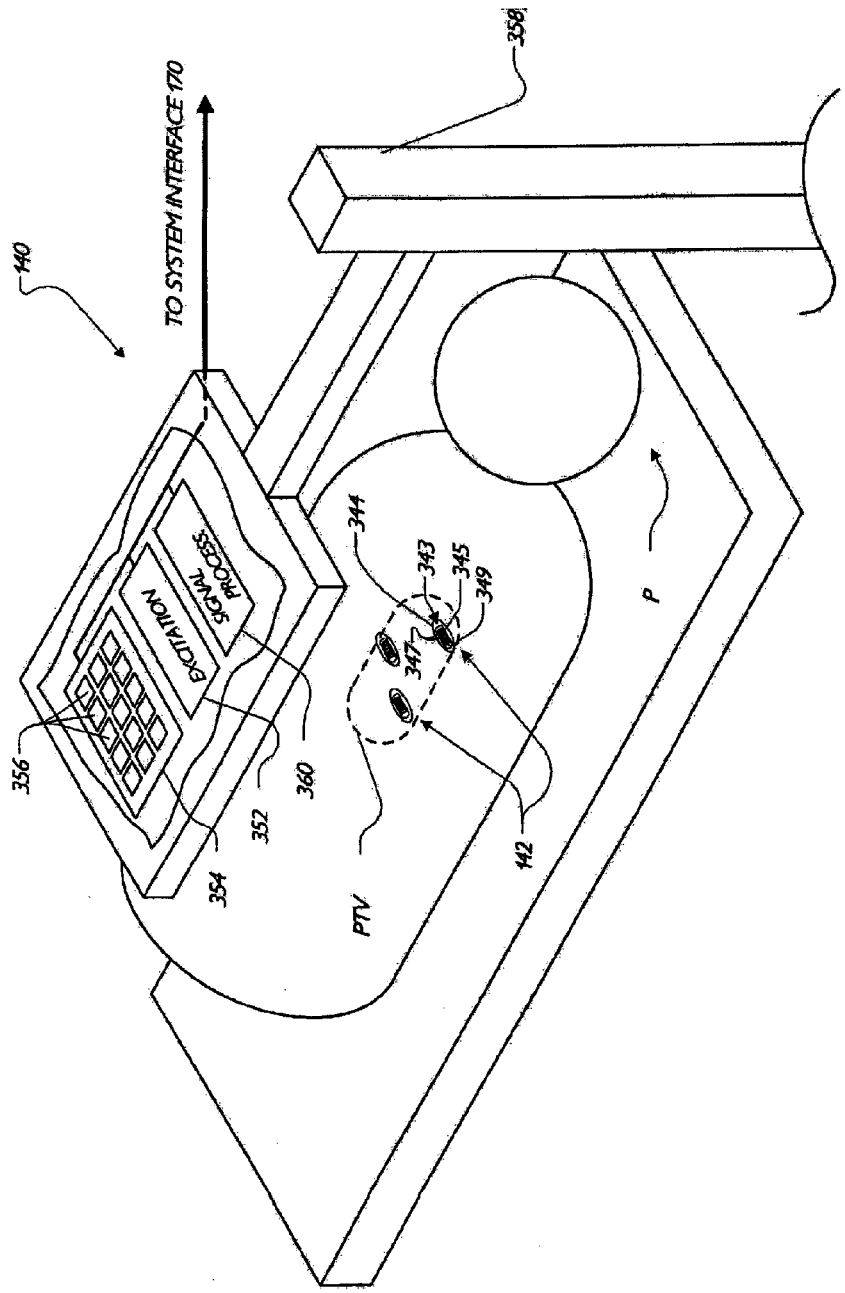
FIG. 3 is an isometric, schematic diagram of the system of FIG. 1 showing an embodiment of a localization subsystem in more detail.
Figure 4:
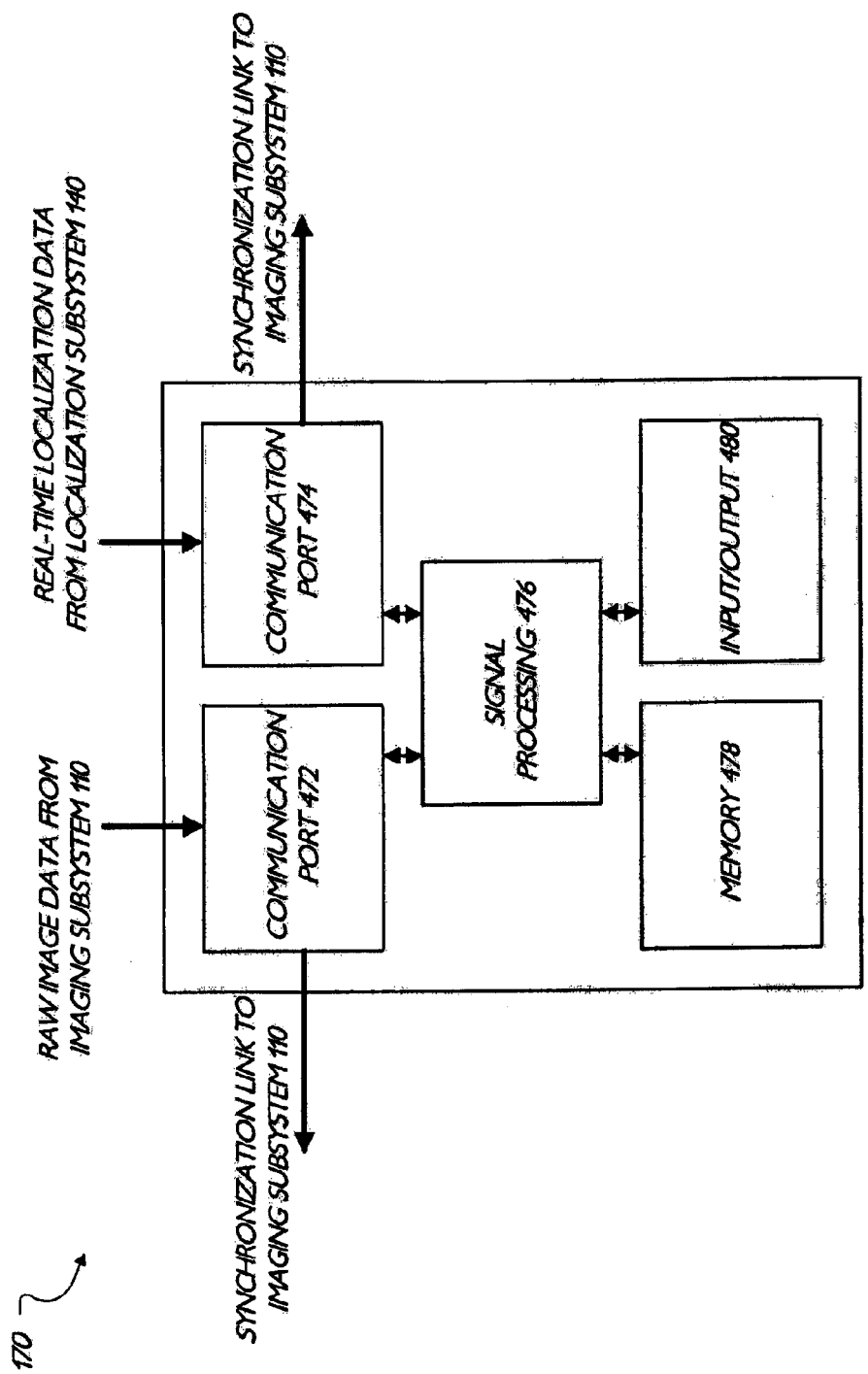
FIG. 4 is a block diagram of the system of FIG. 1 showing an embodiment of a system interface in more detail.

FIGS. 2-4 are schematic diagrams illustrating, respectively, the imaging subsystem 110, the localization subsystem 140, and the system interface 170 of the imaging and localization system 100 in more detail. Referring to FIG. 2, the imaging subsystem 110 can include a gantry 212 having a gantry bore 214, a table or couch 216 for carrying the patient and positioning the patient within the gantry bore 214, and one or more imaging device(s) 218 (drawn in phantom) disposed at or within the gantry 212. For example, the imaging device(s) 218 can include an X-ray source (e.g., a linear accelerator) that freely rotates about a central axis 220 of the gantry 220, as well as X-ray detectors that also rotate about the axis 220 or are stationary.

The imaging subsystem 110 also includes a signal processing unit 230 (drawn in phantom) that is operably coupled with the imaging device(s) 218 for collecting raw image data regarding the PTV of the patient. In general, the signal processing unit 230 can carry out a variety of processing algorithms that assemble or otherwise construct image slices or image frames (based on the image slices), for example, to produce a digitally reconstructed radiograph (DRR). In several embodiments, the signal processing unit 230 can also produce raw image data according to a digital imaging and communication in medicine (DICOM) standard or interface with another system (not shown) that formats data into such a standard. In addition, in many examples, the signal processing unit 230 is also operably coupled with the gantry 212 and/or the table 216 for positioning the imaging device(s) 218 with respect to the PTV. For example, the signal processing unit 230 can be configured to control the rate at which the imaging device(s) 218 rotate and/or the rate at which the table 216 moves through the gantry bore 214. In many embodiments, the configuration of the gantry 212, gantry bore 214, table 216, the imaging device(s) 218, and/or the processing unit 230 is suited for CT-based imaging. However, in other embodiments, other imaging subsystems can include additional or alternative components that are suited for other types of imaging (e.g., fluoroscopic, MRI, PET, or ultrasonic imaging). Furthermore, although not shown in FIG. 2, the signal processing unit 230 can also be coupled with various input/output components (e.g., keyboards, displays, touchscreens, etc.) for allowing an operator to program/control the imaging subsystem 110.

Turning now to FIG. 3, the localization subsystem 140 includes an excitation source 352 and a sensor array 354 of individual sensors or coils 356 spaced apart from one another in a known geometry relative to one another. In many embodiments, the excitation source 352 and the sensor array 354 can be carried by a support apparatus 358, which can in turn position the excitation source 352 and sensor array 354 within the gantry bore 214 (FIG. 2) to detect the location of individual markers 142 (and thus the patient PTV). However, in other embodiments the excitation source 352 and sensor array 354 can be mounted to or otherwise attached to the gantry 212

(FIG. 2). Additional embodiments of the localization subsystem 140 can also include, for example, the excitation sources, sensor arrays, and signal processing components shown and described in U.S. Pat. Nos. 6,977,504 and 7,026,927 and U.S. application Ser. No. 10/749,860, all of which are incorporated herein by reference.

The localization subsystem 140 also includes one or more signal processing/control components 360 that can be integrated into a common assembly with the excitation source 352 and sensor array 354 and/or can be incorporated into a stand-alone operator interface (not shown). In general, the signal processing/control components 360 are configured to (a) use the excitation source 352 to wirelessly deliver a pulsed magnetic field to energize individual markers 142, (b) receive a location signal from the individual markers 142 via the sensor array 354, and (c) periodically calculate a location of the individual markers 142 in a reference frame. Because the individual sensors 356 of the sensor array 354 are spaced apart from one other in a known geometry relative to each other, the absolute location of the individual markers can be determined by a known location (e.g., a known location of one of the sensors 356 or another external sensor). The dimensionality of localization, alignment and/or registration of the PTV can be determined based on the known location and the number of active markers deployed at or adjacent the PTV. For example, a single marker defines a single position in localization space; two markers can be used to register the distance between two points. Furthermore, two independent sets of two markers attached to soft tissue can be used to register and align two vectors relative to each other. And, three markers attached to soft tissue relative to each other can be used to define a plane including rotational angles of the plane (i.e. pitch, yaw and roll). A variety of processing algorithms can provide such a determination, examples of which are set forth in U.S. application Ser. Nos. 10/679,801; 10/749,478; 10/750,456; 10/750,164; 10/750,165; 10/749,860; and 10/750,453, all of which are incorporated herein by reference.

In many applications, active markers can be directly affixed to the PTV or to organs or tissues adjacent the PTV. For example, in applications that image portions of the lungs or lung tumors, a bronchoscope along with visual and fluoroscopic guidance can be used to direct a guide wire to bronchi locations. The guide wire can be used to wedge the individual markers as distally as possible to maximize fixation of the markers within the lungs. In many embodiments, such techniques are minimally invasive, and can position the markers as close as possible to the PTV without employing more invasive techniques. In other embodiments, however, other types of procedures may be used to position the markers at the PTV (e.g., laparoscopic implantation).

Embodiments of the individual marker 142 can include a transponder 343 contained in a biocompatible capsule 344 and having a core 345, a coil 347 around the core 345, and a capacitor 349 electrically coupled to the coil 347. The core 345 is typically composed of ferrite, and the coil 347 includes a plurality of windings of a wire around the core 345. The transponder 343 is a resonating circuit that receives the wirelessly transmitted magnetic excitation energy and produces a wirelessly transmitted location signal in response to the excitation signal. The transponder 343 accordingly has a resonant frequency at which the magnetic excitation energy energizes the transponder 343. In many embodiments, individual markers 142 can have transponders having resonant frequencies that are different from one another (e.g., for signal discrimination). Embodiments of suitable markers can also include, for example, the markers shown and described in U.S. Pat. Nos. 7,135,978, 6,918,919 and 6,822,570; U.S. application Ser. Nos. 10/334,700; 10/679,801; 10/382,123; 10/745,097; 10/746,888; and 11/166,801, all of which are incorporated herein by reference.

Referring now to FIG. 4, the system interface 170 can include communication ports 472 and 474, at least one signal processor 476 operably coupled to the communication ports 472 and 474, and a memory 478 storing processing instructions that are executable by the processor 476. The one or more communication ports 472 are operably coupled with the imaging subsystem 110, the one or more communication ports 474 are operably coupled with the localization subsystem 140, and the signal processor 478 can process data received at these ports (i.e., raw image data and real-time localization data) based on the processing instructions stored at the memory 478. In many embodiments, the system interface 170 also includes input/output components 480 (e.g., a keyboard, mouse, display, printer), which, for example, can allow an operator of the system interface 170 to (a) edit or modify image data, (b) control data processing, and/or (c) view graphical or numeric output corresponding to raw image data, real-time localization data, and/or motion-compensated image data.

Embodiments of the system interface 170 can also include a synchronization link 482 and/or a feedback link 484 between the system interface 170 and the imaging subsystem 110. The imaging subsystem 110 can communicate a synchronization signal over the synchronization link 482, and the system interface 170 can communicate a feedback signal over the feedback link 484. In many examples, the synchronization signal can be used by the system interface 170 to align raw image data with real time localization data. For example, to compensate for respiratory motion, a synchronization signal can create a time indicator as to when a patient's lungs are fully inhaled and/or fully exhaled. Accordingly, the real-time localization data can then be correlated with the phase of a patient's breathing cycle based on this time indicator. The feedback signal, on the other hand, can be used by the system interface 170 to communicate with the imaging subsystem 110. For example, if the PTV location shifts out of detection range (or in some other type of manner), the system interface 170 can use the feedback signal to alert the imaging subsystem 110 that such a shift has occurred. The imaging subsystem 110 can accordingly halt operation or adjust image processing (at the processing unit 230) based on the feedback signal.

In other, non-illustrated embodiments, the system interface 170 can be a simple communication link between the imaging subsystem 110 and localization subsystem 140. In several embodiments, the imaging subsystem 110 and the localization subsystem 140 can be configured to communicate signals and transmit data between one another. For example, the processing unit 230 (FIG. 2) of the imaging subsystem 110 could receive real-time localization data from the localization subsystem 110 and use such data in the processing or assembly of image slices or image frames. Additionally or alternatively, the processing unit 230 could also use the real-time localization data to gate one or more of the imaging devices 218 (FIG. 2).

FIG. 5 is a flow diagram showing an embodiment of operating the imaging and localization system 100. The method first includes implanting one or more active markers at a patient PTV (block 500) and positioning the PTV within proximity of the imaging and localization subsystems (block 502). Next, the localization subsystem tracks the location of the PTV (blocks 510-516) and the imaging subsystem scans (and images) the PTV (block 520 and 522). To track the location of the PTV, the localization subsystem uses the excitation source to excite the individual markers (block 510), and detects the location of the markers by "listening" for the location signal (block 512). The localization subsystem can then generate real-time localization data using these location signals (block 514) and communicate the real-time localization data to the system interface (block 516). Concurrent with the location tracking, the imaging subsystem produces raw image data frames regarding the PTV (block 520) and communicates this data to the system interface (block 522). The system interface, in turn, processes the raw image data based on the real-time localization data (block 530).

In one embodiment, the system interface bins raw image data (or image slices or frames) based on the real-time location of the PTV and outputs motion-compensated image data corresponding to a particular subset of the binned image data. For example, the raw image data can be binned (or filtered) based on a range of locations associated with the PTV (described further with reference to FIG. 6). Additionally or alternatively, the binning of the raw image data can be further based on a specific time or window in patient's breathing cycle (e.g., determined by a synchronization signal). In other embodiments, the system interface can employ other types of image processing. For example, in addition to or in lieu of binning the imaging frames, the system interface can adjust or calibrate the processing algorithm of the imaging subsystem based on the real-time localization data of the localization subsystem. In such an example, the system interface 170 could use the feedback link 484 (FIG. 4) to provide an adjustment or calibration.

FIG. 6 is a flow diagram showing an embodiment of binning raw image data in more detail. The method first includes identifying location datums within the real-time localization data of the localization subsystem (block 600). For example, individual location datums can include a time stamp and spatial coordinates (e.g., 2-dimensional or 3-dimensional) regarding an individual marker. Next, one or more sets of these datums are associated with individual sets of raw image data produced by the imaging subsystem (block 602). The individual sets of raw image data are then binned based on the location datums (block 604). For example, individual sets of raw image data can be binned based on a specific window of time stamp values and/or a specific window of spatial coordinates attributed to each of the sets of raw image data. After binning the individual sets of raw image data, a subset of the raw image data can be output as motion-compensated image data (block 606).

C. Imaging Subsystems

Described below are examples of various imaging subsystems that can be employed with the imaging and localization system 100. In general, the imaging subsystems described below are CT based imaging systems. However, it is contemplated that other types of imaging subsystems can be employed within embodiments of the imaging and localization system 110, for example, such as those that use other types of radiographic and non-radiographic imaging techniques (e.g., digital tomosynthesis, fluoroscopic, MRI, and/or ultrasonic imaging).

In general, CT imaging methods include employing an X-ray source and detector to scan a patient PTV at a target depth. In many examples, portions of the anatomy adjacent a PTV can be blurred-out of an imaging frame by implementing a variable depth of field between an X-ray source and detector. An imaging frame of a PTV, accordingly, is sharp and detailed, and well contrasted against background anatomy. As described above, modern methods of CT imaging are generally carried out by rotating an X-ray source about a central axis of a gantry bore and using a detector (either stationary or rotating) on an opposite side of the PTV to acquire multiple image "slices" of a PTV. These image slices can accordingly be assembled based on a variety of processing algorithms to produce an image frame.

Embodiments of the imaging subsystem can employ a variety of CT image acquisition techniques, including axial, helical or spiral, or cine CT techniques. In axial CT, a patient table is stationary while an X-ray source rotates (and optionally a detector) about the PTV to acquire image slices. The table can be subsequently moved, and additional image slices can be acquired after the table returns to a stationary position. Such slices can be assembled or aggregated to create a volumetric representation of a PTV. Helical CT is similar to axial CT, but moves the patient smoothly through the gantry bore while concurrently rotating the X-ray source. Helical CT scans are advantageous in that a large patient volume can be acquired in about 20-60 seconds. In addition, Helical CT scans do not have an interscan delay that normally occurs when repositioning the table in axial CT. Ciné CT, on the other hand, produces a time sequence of axial images, and is generally used when the temporal nature of a PTV is important (e.g., to evaluate blood flow).

Additionally, other embodiments of CT systems can further include multislice and/or dual source systems. Multislice CT scanners can employ axial or helical imaging techniques, but are configured to include more than one detector. In general, increasing the number of detectors allows increased x-ray source rotation speeds. For example, modern multislice CT systems can include up to 256 detectors, creating up to 256 corresponding slices (simultaneously). Dual source CT systems can similarly employ axial or helical imaging techniques, but have an increased temporal resolution attributed to a reduction in rotation angle required to acquire a complete image. In addition, dual source CT can employ dual energy imaging, which can be used to differentiate between anatomy that would otherwise be unobtainable differentiable with a single source CT system. For example, dual source CT systems may be used to enhance the differentiation between tumors and adjacent tissues.

Embodiments of CT systems that can be incorporated into the imaging subsystem can also include, for example, the SOMATOM™ CT systems manufactured and sold by Siemens AG.

D. Compatibility of Localization Subsystem with Radiation Delivery Devices

In many embodiments, the localization subsystem 140 is used in proximity to a radiation delivering imaging device (e.g., a linear accelerator) of the imaging subsystem 110. Accordingly, aspects of the imaging and localization system 100, and particularly, the localization subsystem 140 may be adversely interfered with by the operation of such a radiation delivery device (not only the emitted radiation, but the circuitry of the delivery component itself). Therefore, the system 100 can be adapted to mitigate adverse influences attributed to the radiation delivery device.

As one example, components of the localization subsystem 140 (e.g., the excitation source, sensor array 354, and signal processing components 360) can be arranged so that radiation does not travel through the localization subsystem 140. For example, referring to FIG. 2, the excitation source 353, the sensor array 354 and/or the signal processing components 360 can be mounted to the gantry 212 and configured to rotate concurrently with the imaging device(s) 218 such that components of the localization subsystem 140 are never in the line of site of radiation delivering devices.

As another example, the localization subsystem 140 can include a matched filter or other device that can detect the presence of interference due to the operation of radiation delivering devices, or any other interfering device that operates in a pulsed mode. If such interference is detected, the localization subsystem 140 can be operative to discard received location signals that occurred in that timeframe. Additionally or alternatively, the localization subsystem 140 can also include radiation hardened circuitry that is generally impervious to ionizing radiation (below a threshold level). Referring again to FIG. 2, many of the circuit elements of the excitation source 352, sensor array 354, and/or the signal processing components 360 can be manufactured using a variety of radiation hardened techniques and design rules. For example, there are many known techniques in the aerospace industry for mitigating single event transients (SETs), single event upsets (SEUs), or other soft errors that would otherwise occur in the presence of radiation.

E. Experimental Analysis

FIGS. 7-14 are various plots and images showing results of an experimental study that evaluated the performance of motion-compensated CT imaging. More specifically, the experimental study evaluated tumor correlated computed tomography TCCT imaging on a phantom model of respiratory motion. The goals of this study were to 1) simultaneously electromagnetically track and CT scan active markers, 2) read and synchronize data from the subsystems, and 3) select appropriate images for reconstruction. The experimental study was carried out using an active marker-based localization system, embodiments and examples of which have been described above.

1. Experimental Setup

An active marker was embedded in wax, placed adjacent to a 2 cm diameter acrylic ball and the two objects placed on a 4D Phantom stage. The 4D Phantom was placed on the table of a CT scanner (Brilliance CT Big Bore Scanner—Philips, Andover, Mass.) and moved in a trajectory recorded from a canine breathing study that was performed using variable forced ventilation. The sensor array of the localization subsystem was placed over the 4D Phantom stage in the gantry bore. A real-time location signal was generated that was synchronized to the CT acquisition while the CT scans were acquired and the localization sub-system monitored the active marker position The CT scanner was operated in a ciné axial mode with 15 acquisitions per table position. Each image was created with a 0.44 second rotation time followed by a 0.5 second dead time. Each table position contained 16 contiguous 1.5 mm thick for a total of 2.4 cm width. There was a 2-4 s pause between adjacent table position acquisitions.

2. Localization Subsystem Performance Measured by 4D Phantom

Figure 8:
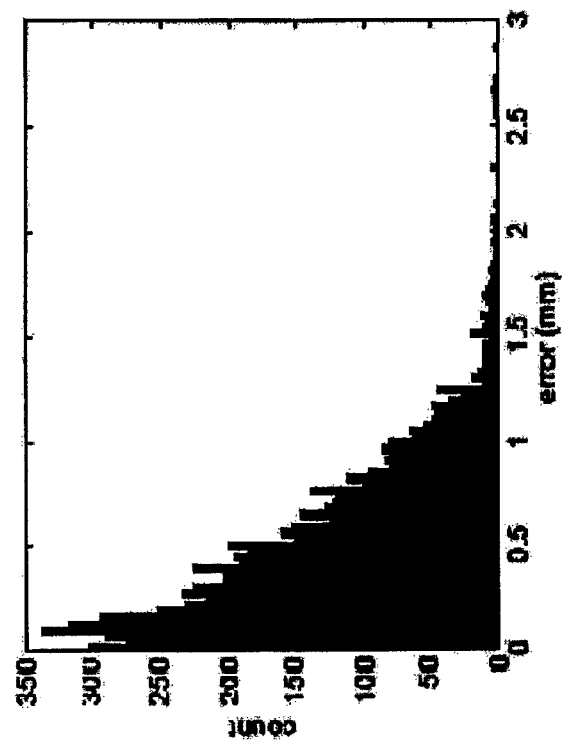
FIGS. 7-14 are various plots and images showing results from an experimental study that evaluated the performance of motion-compensated computed tomography (CT) imaging.
Figure 7:
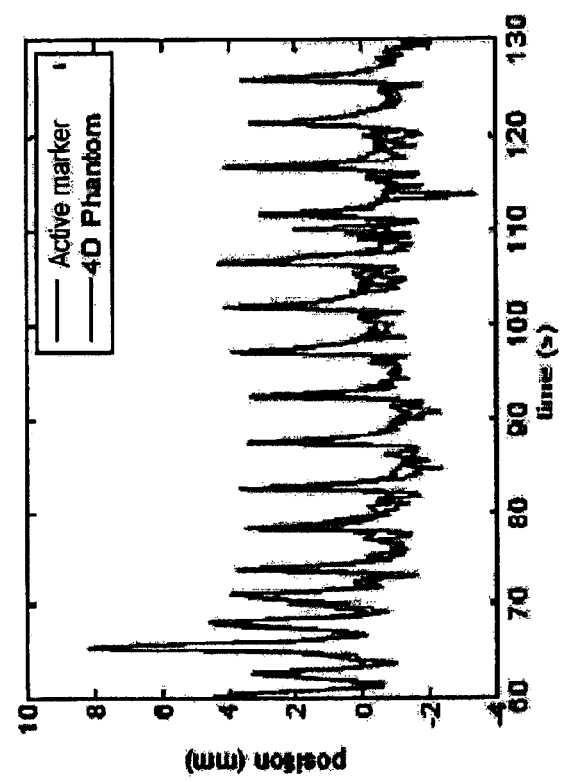

The accuracy of the localization sub-system in a CT scanner environment was determined by comparing the real-time localization data output to 4D Phantom position. FIG. 7 is a plot showing the analysis of motion of an active marker location and the 4D phantom location in the vertical direction. FIG. 8 is a plot showing the localization sub-system's RMS localization error was 0.6 mm, slightly greater than when the localization subsystem was run outside of the CT, but still acceptable for clinical applications.

3. Image Data Processing

Figure 9:
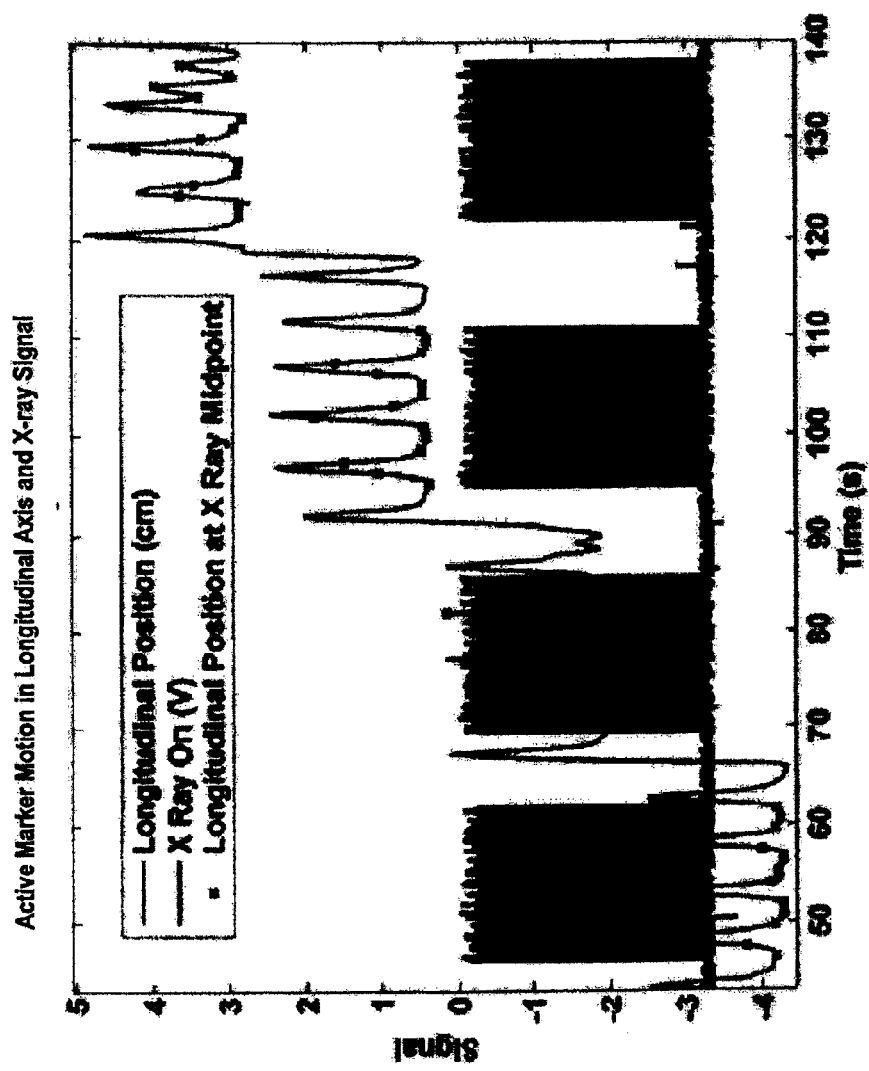
Figure 10:
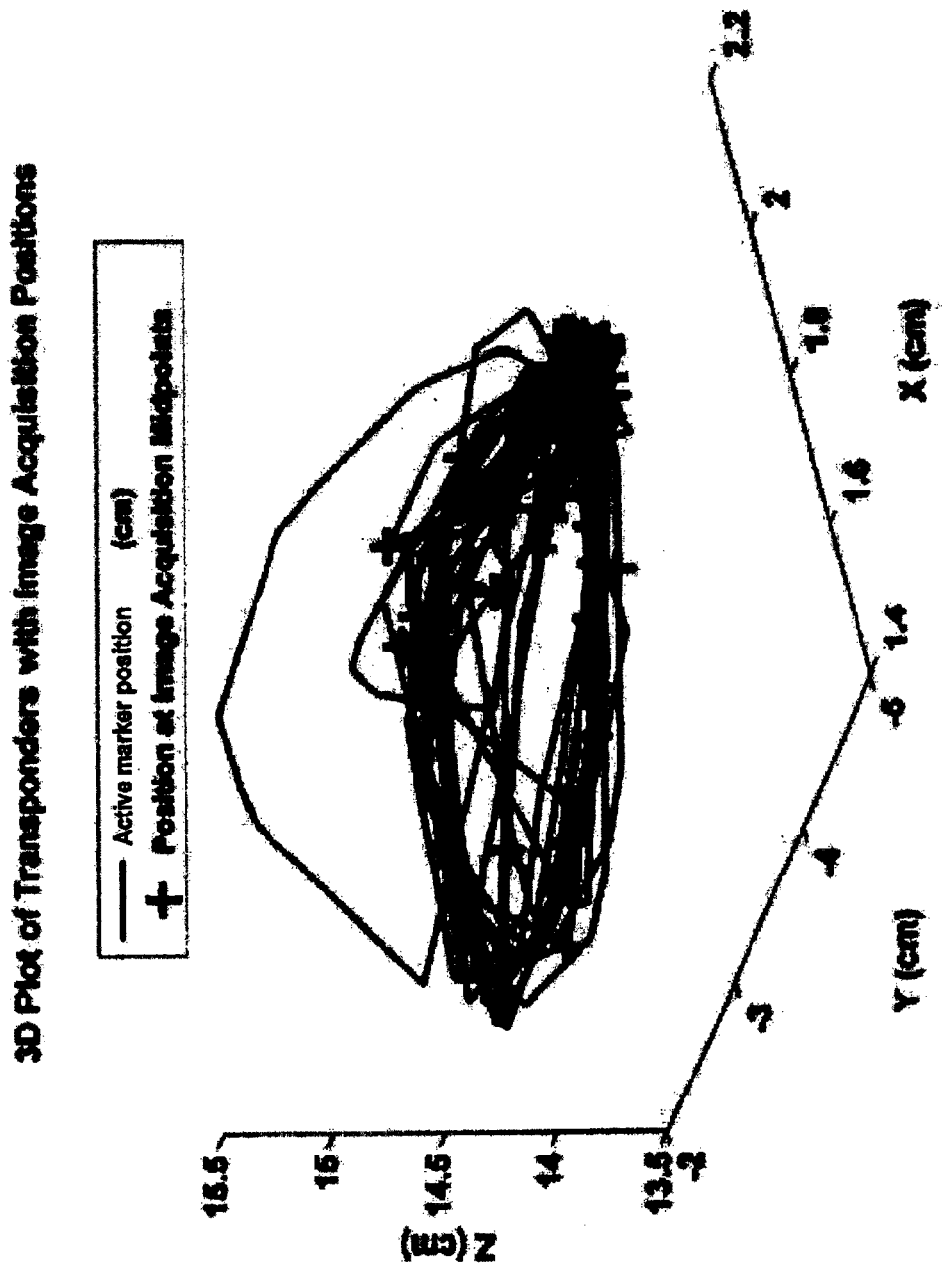

Active marker positions were successfully synchronized with the CT images. The longitudinal (in/out of table) position and the associated x-ray on signals from the CT table are shown in FIG. 9. In FIG. 9, the active marker positions at the midpoints of the X Ray On signals are represented by x's superimposed on the active marker position curve, and the change in longitudinal baseline with each set of pulses represent the table movement in between different table positions. FIG. 10 shows the 3D active marker position over the study. The active marker positions at the midpoints of the X Ray On signals are represented by crosses.

Figure 11:
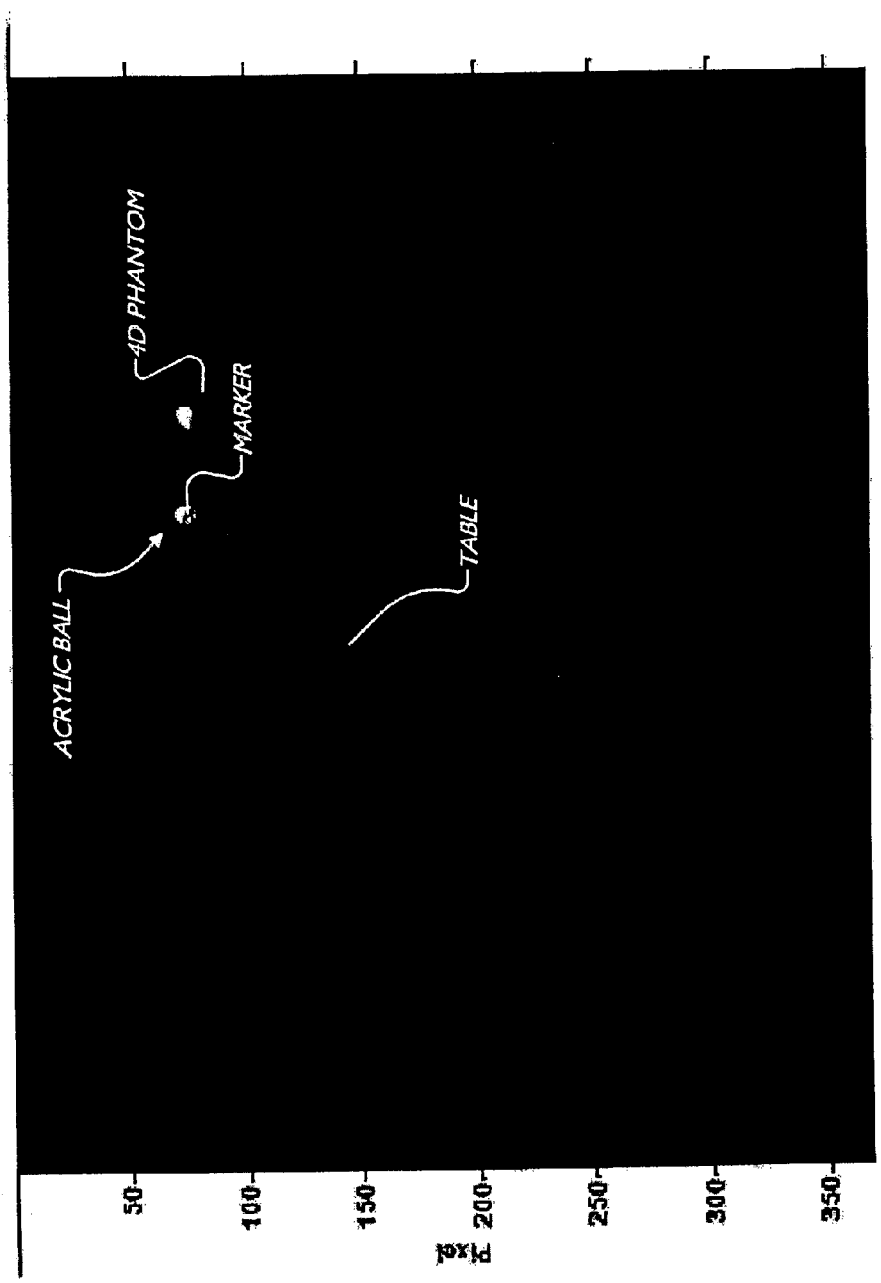
Figure 12:
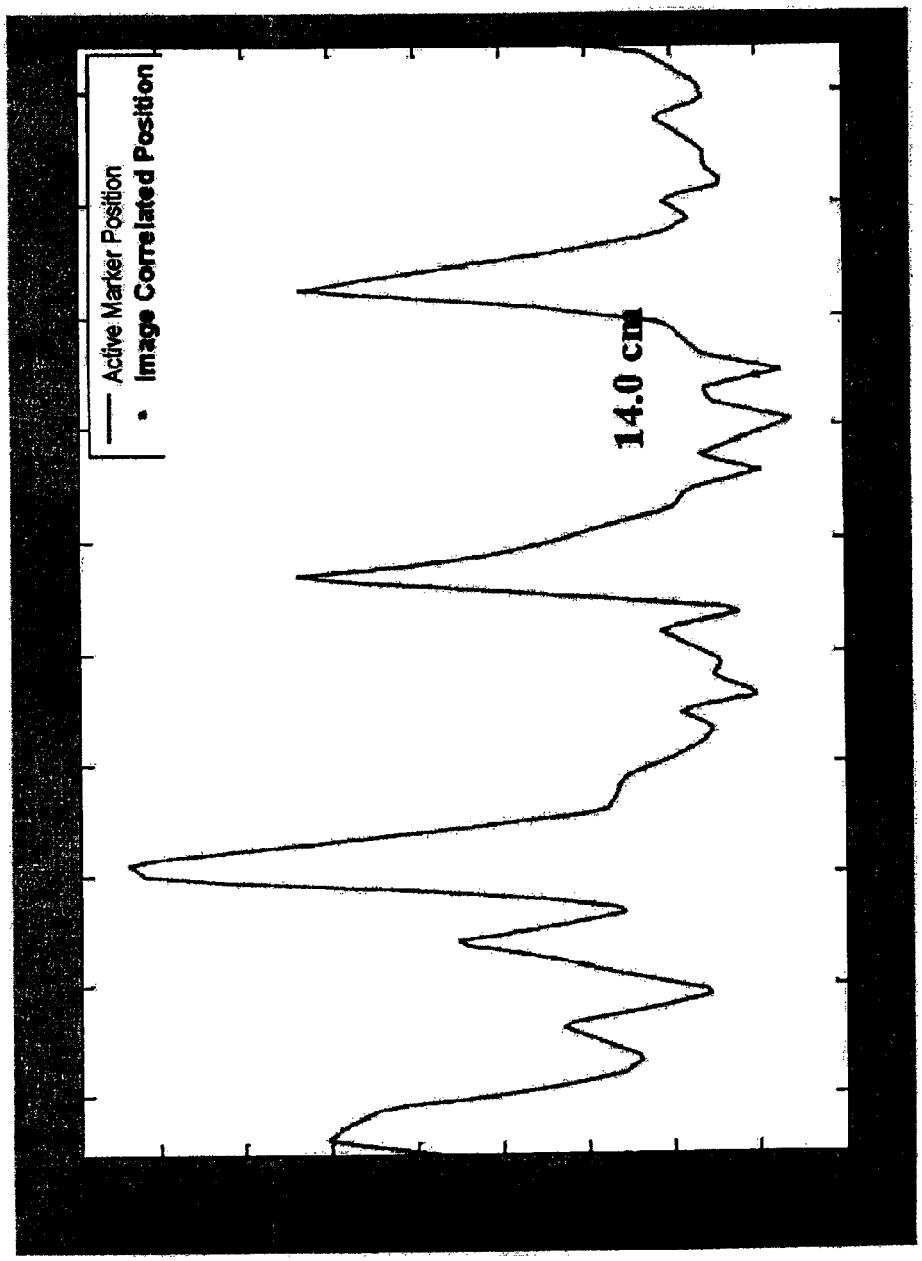
Figure 14:
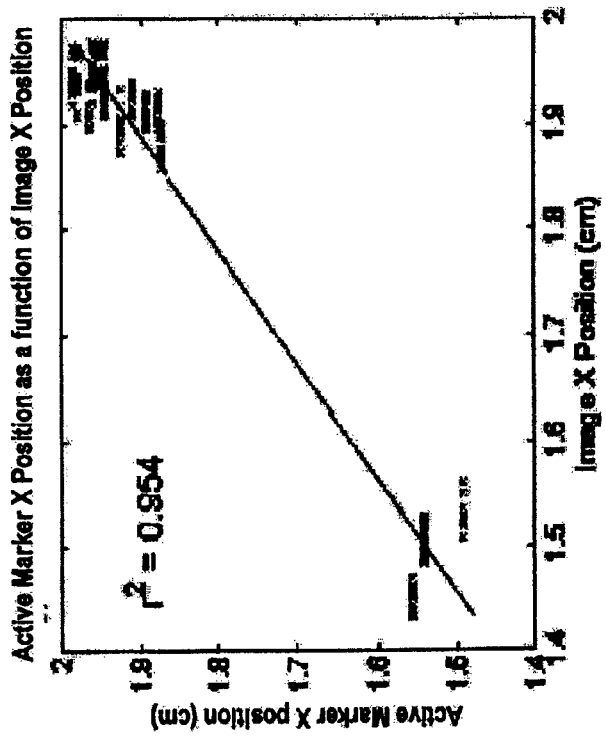
Figure 13:
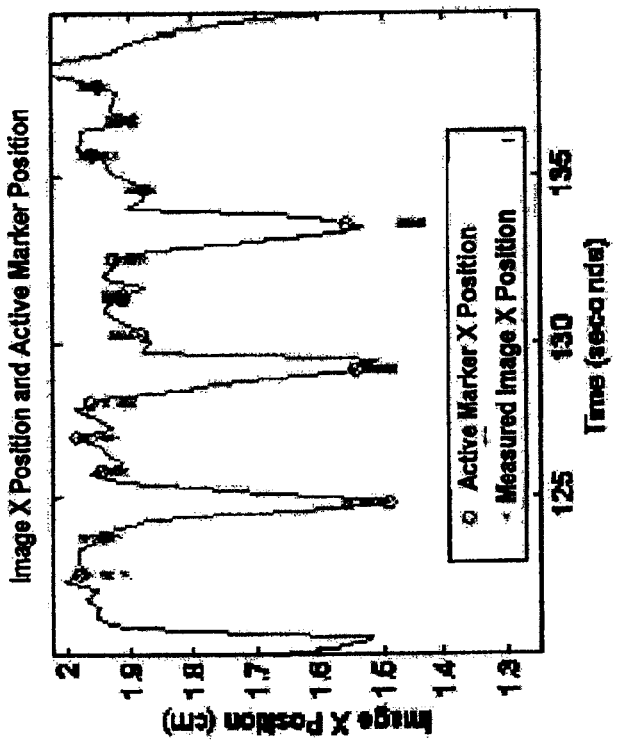

The CT image frames were binned with respect to the measured active marker position. A sample transverse image and its corresponding active marker trace are shown in FIG. 11. A feature mapping program was written in Matlab to assess the center of the stage in each image for the fourth table position. FIG. 12 is a plot showing the lateral locations of the stage compared against the localization subsystem-measured lateral coordinates for each of the 240 images acquired at one of the table positions. The correlation coefficient is 0.954, consistent with the precision of the localization subsystem in the CT environment. FIGS. 13 and 14 are plots showing the CT image frame lateral positions and the active marker lateral positions versus time and plotted against each other. Note spread of image locations corresponds to limits of image processing algorithm of the CT scanner.

F. Conclusion

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art.

The various embodiments described above can be combined to provide further embodiments. For example, aspects of the system interface 170 can be omitted or incorporated into one or both of the imaging and location subsystem (e.g., the communication ports 472 and 474, the processor 476, and the memory 478). In addition, in other embodiments, the system interface 470 can be used more generally to provide a communication link between the imaging and localization subsystems 110 and 140. Further, all the U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of this disclosure and referenced disclosures can be modified, if necessary, to employ systems, devices, and concepts of the various patents, applications, and publications to provide yet further embodiments.

These and other changes can be made to various embodiments in light of the above-detailed description. In general, in the following claims, the terms used should not be construed as limiting the specific embodiments disclosed in the specification and the claims, but should be construed to include all imaging and localization subsystems (and aspect thereof) that operate in accordance with the claims to provide systems and methods for imaging a selected target volume within a patient based on the real-time location of one or more active markers. Accordingly, the invention is not limited, except as by the appended claims.

We claim:

1. A system for producing image data regarding a planning target volume (PTV) within a patient's body, the system comprising:
    at least one marker that is implantable at the PTV within the patient;
    sensors positioned to receive an electromagnetic location signal that is broadcast by the active marker, the sensors being spaced apart from each other in a known geometry relative to each other;
    a signal processing component configured to produce real-time localization data corresponding to the location signal based on the known geometry, the real-time localization data including a plurality of time stamps and spatial coordinates associated with a corresponding one of the time stamps; and a system interface operably coupled with the signal processing component, the system interface also being operably coupled with an imaging system that scans the PTV to produce raw image data regarding the PTV, wherein the imaging system uses a processing algorithm to construct at least one of image frames and image slices, and wherein the system interface is configured to
concurrently receive both the real-time localization data from the signal processing component and raw image data from the imaging system while it simultaneously scans the PTV,
bin the raw image data based on a specific window of the real-time location data while the imaging system is still scanning the PTV,
output motion compensated image data corresponding to a particular subset of the binned raw image data,
detect a change in location of the PTV out of a detection range based on the real-time localization data, and
in response to detecting the change in location of the PTV, direct the imaging system to adjust image processing by calibrating the processing algorithm as it is still scanning the PTV.

2. The system of claim 1 wherein the system interface is further configured to provide a feedback signal to the imaging system, the feedback signal configured to adjust the algorithm for constructing the at least one of the image frames and the image slices.

3. The system of claim 1 wherein the PTV includes a portion of a lung or a tissue adjacent the lung.

4. The system of claim 3 wherein the marker is implanted at the bronchi of a lung.

5. The system of claim 1 wherein the system further comprises an excitation source for transmitting excitation energy, and wherein the marker further comprises a wireless transponder configured to wirelessly transmit the location signal in response to the excitation energy.

6. The system of claim 1 wherein the system interface is operably coupled with a computed tomography (CT) imaging system, the CT imaging system producing the raw image data.

7. A system for creating motion-compensated image data regarding an interior and volumetric portion of a patient, comprising:
an imaging subsystem that scans the volumetric portion to produce raw image data regarding the volumetric portion and uses a processing algorithm to construct at least one of image frames and image slices;
markers fixable at a position located at the volumetric portion and being excitable to produce an identifiable marker signal, the markers being spaced apart from each other in a known geometry relative to each other;
sensors and one or more associated signal processing/control components that detect the identifiable marker signal and output real-time localization data based on the identifiable marker signal and the known geometry while the imaging system scans the volumetric portion, the real-time localization data including a plurality of time stamps and spatial coordinates associated with a corresponding one of the time stamps; and
a processor that processes the raw image data by binning the raw image data while the imaging subsystem scans the volumetric portion, the binning being based, at least in part, on a specific window of the time stamps and the corresponding spatial coordinates, the processor being operably coupled with the imaging subsystem, the sensors, and the associated signal processing/control components of the sensors,
wherein the processor outputs motion compensated image data corresponding to a particular subset of the binned raw image data, and
wherein the processor detects a change in location of at least one of the active markers out of a detection range based on the spatial coordinates the processor receives while the imaging system simultaneously scans the volumetric portion, and wherein the processor directs the imaging subsystem to adjust image processing by calibrating the processing algorithm in response to detecting the change in location while the imaging system is still scanning the volumetric portion.

8. The system of claim 7 wherein the markers comprise a first magnetic transponder having a first resonant frequency and a second magnetic transponder having a second resonant frequency different than the first resonant frequency.

9. The system of claim 7, wherein the imaging subsystem further comprises:
a source device positioned to deliver X-ray radiation to the volumetric portion;
a detector device positioned to receive at least a portion of the X-ray radiation; and
a processing unit coupled to the detector device for producing the raw image data based on received X-ray radiation.

10. The system of claim 9 wherein the system further includes a gantry for carrying the source device and the detection device, the gantry being configured to at least partially rotate at least one of the source and the detection device about the volumetric portion of the patient.

11. The system of claim 10 wherein the gantry also carries the sensors, and is configured to rotate the sensors concurrently with the source device so that the X-ray radiation does not pass through the sensors.

12. A method for eliminating motion artifacts in an imaging system, the method comprising:
receiving time-varying localization data from a sensor array in communication with a plurality of active markers disposed within a patient's body, the sensor array being located outside the patient, the plurality of active markers being spaced apart from each other in a known geometry relative to each other, and the time-varying localization data being based on the known geometry;
concurrent to receiving the localization data, scanning a volumetric portion of the patient's body to produce raw image data regarding the volumetric portion, the volumetric portion including the active markers or the active markers being at the volumetric portion; and
while scanning the volumetric portion
processing the raw image data into image frames regarding the volumetric portion using a processing algorithm to produce image frames,
binning the image frames based on a specific window of the real-time localization data, the real-time localization data including a plurality of time stamps and spatial coordinates associated with a corresponding one of the time stamps,
outputting motion compensated image data corresponding to a particular subset of the binned raw image data,
detecting a shift in location of the volumetric portion out of a detection based on the localization data, and calibrating the processing algorithm in response to detecting the change in location of the volumetric portion.

13. The method of claim 12 wherein the image frames are produced by a computed tomography scanner.

14. The method of claim 12 wherein the localization data comprises individual datums that include a time stamp and two-dimensional or three-dimensional spatial coordinates.

15. The method of claim 12 wherein the localization data is first localization data, and wherein the method further comprises synchronizing the second localization data with the raw image data prior to processing the image frames based on the first localization data.

16. The method of claim 12 wherein the raw image data is produced by an imaging system, and wherein the method further comprises providing a feedback signal to the imaging system, the feedback signal being based, at least in part, on the localization data.

17. The method of claim 12 wherein volumetric portion includes a portion of the lung, a tumor adjacent the lung, or both.

18. A method, comprising:
  implanting markers at or adjacent a planning target volume (PTV) within a patient's body, the markers being spaced apart from each other in a known geometry relative to each other;
  exciting the markers to produce an excitation signal;
  detecting, in real time, a location of the markers based on the known geometry using an array of sensors positioned to receive the signal;
  associating a time stamp with each of the detected real-time locations;
  concurrently receiving the time stamps and associated real-time locations and scanning the PTV using a computed tomography (CT) imaging system, wherein scanning the PTV includes acquiring raw image data regarding the PTV and processing the raw image data into frames using an algorithm; and
  as the CT imaging system acquires the raw image data
    providing the image frames to a system interface for binning the image frames in real time, the binned image frames being based on a specific window of the detected real time location of the markers and the time stamp associated with each of the detected real time locations,
    outputting motion compensated image data corresponding to a particular subset of the binned image frames,
    receiving a feedback signal at the CT imaging system from the system interface indicating that the PTV has shifted out of a detection range, and
  modifying the processing of the raw image data by calibrating the algorithm based on the feedback signal.

19. The method of claim 18 wherein the CT imaging system includes an axial CT, a helical CT, or a ciné CT scanner.

20. The method of claim 18, further comprising using the filtered or binned image data for a medical diagnosis or medical procedure planning.

21. The method of claim 18 wherein individual markers comprise an electromagnetic transponder.

* * * * *